(12) United States Patent
Mueller, Jr.

(10) Patent No.: US 7,316,654 B2
(45) Date of Patent: Jan. 8, 2008

(54) ILLUMINATED NIPPLE CUP

(75) Inventor: Richard L. Mueller, Jr., Jackson, WY (US)

(73) Assignee: Acueity, Inc., Hayward, CA (US)

( * ) Notice: Subject to any disclaimer, the term of this patent is extended or adjusted under 35 U.S.C. 154(b) by 521 days.

(21) Appl. No.: 10/351,058

(22) Filed: Jan. 24, 2003

(65) Prior Publication Data

US 2004/0147813 A1    Jul. 29, 2004

(51) Int. Cl.
*A61B 10/00* (2006.01)
(52) U.S. Cl. .................................................. 600/562
(58) Field of Classification Search ................ 600/562, 600/38, 121, 123, 157, 156; 604/19–21, 604/74, 113, 514; 607/89; 601/14
See application file for complete search history.

(56) References Cited

U.S. PATENT DOCUMENTS 5,445,608 A * 8/1995 Chen et al. .................... 604/20
5,575,756 A * 11/1996 Karasawa et al. ............ 600/157
6,328,709 B1 * 12/2001 Hung et al. ..................... 604/74
6,358,226 B1 * 3/2002 Ryan ............................. 604/74
6,500,112 B1 * 12/2002 Khouri ........................... 600/38

* cited by examiner

Primary Examiner—Max F. Hindenburg
Assistant Examiner—Brian Szmal
(74) Attorney, Agent, or Firm—Olson & Cepuritis, Ltd.

(57) ABSTRACT

A device suitable for viewing and illuminating a mammary duct orifice comprising a hollow receptacle defining an interior volume and an open aperture at a distal end thereof sized to circumscribe the nipple. The open aperture preferably is surrounded by an outwardly extending flange that can be provided with an adhesive. A vacuum port suitable for connection to a vacuum source to create a vacuum in the interior volume may also be configured as part of the hollow receptacle. An illumination source is provided within the device to illuminate nipple orifices when a nipple is positioned within the hollow receptacle.

17 Claims, 3 Drawing Sheets

ILLUMINATED NIPPLE CUP

TECHNICAL FIELD OF THE INVENTION

The invention relates to a medical apparatus for viewing and identifying ductal orifices.

BACKGROUND OF THE INVENTION

Breast cancer is one of the health threats most feared by women, and is the most common form of cancer in women. A key to treatment is early detection. For example, an annual mammogram is a method that has been used in hopes of early detection of breast cancer. One problem with mammography is that such an imaging technique can only find breast cancer once it has taken form. All too often, breast cancer is discovered at a stage that is too far advanced, when therapeutic options and survival rates are severely limited. As such, more sensitive and reliable methods and devices are needed to detect cancerous, pre-cancerous, and other cancer indicators of the breast at an early stage. Such methods and devices could significantly improve breast cancer survival. While breast cancer is most common among women, in rare instances the human male may also have occurrences of breast cancer.

Other methods of detecting breast cancer are based on the fact that a vast majority of instances of breast cancer begins in the lining of mammary ducts. Studies have shown that fluid within the mammary duct contains high levels of breast cancer markers, and that an estimated 80%-90% of all breast cancers occur within the intraductal epithelium of the mammary glands. Fluid within the breast ducts contains an assemblage and concentration of hormones, growth factors and other potential markers comparable to those secreted by, or acting upon, the surrounding cells of the alveolar-ductal system. Likewise, mammary fluid typically contains cells and cellular debris or products that can also be used in cytological or immunological assays.

A typical breast nipple contains about 8 to about 12 orifices that are external termini of the mammary ducts through which milk and other mammary fluid flow during lactation, for example. The orifices are each surrounded by a sphincter muscle which normally keeps the ducts closed. Application of pressure posterior to the periphery of the sphincter muscles can cause the muscles to open. Samples of mammary fluid and/or mammary duct cells can be collected for analysis by expressing the fluid in the mammary duct, or by utilizing a vacuum assist device to draw fluid from the mammary duct. Another way to obtain samples of the contents of a mammary duct is through ductal lavage.

In many instances, a clinician may desire to take samples from the same duct over a period of time. This requires that the clinician be able to find the same duct repeatedly. A difficulty, however, often arises in identifying the particular mammary duct terminating at a nipple orifice that is yielding the sample fluid because of the relatively small size and natural irregular surface of the nipple. The present invention fulfills this need.

Prior developments have included integration of a magnifying lens to a device to aid in identification of a discharging nipple. An example of such a device is disclosed by U.S. Pat. No. 6,328,709, issued to Hung et al. In practice such an approach, however, typically falls short of generating the desired results. For example, typical mammary duct examinations require a number of procedures requiring identification and location of a particular nipple orifice. As such, a physician typically utilizes a head-mounted magnifying glass, thereby making an integrated magnifying lens unnecessary. Devices, such as that disclosed in aforementioned U.S. Pat. No. 6,328,709, are also problematic for the further reason that nipple heights among patients can vary substantially. As such the particular focal length of a magnifying lens may not be suitable for the nipples to be examined. Moreover, by their nature, magnifying lenses cause distortion of the image viewed.

The present invention overcomes the problems encountered with the prior art and provides an improved device for viewing and identifying mammary duct orifices.

SUMMARY OF THE INVENTION

A device suitable for viewing and illuminating a mammary duct orifice comprises a hollow receptacle defining an interior volume and having an open distal end sized to circumscribe the nipple. The open end terminates in an aperture defined by a rim of the receptacle. A vacuum port, which is suitable for connection to a vacuum source to create reduced pressure in the interior volume, may also be configured as part of the hollow receptacle. An illumination source to illuminate nipple orifices while a nipple is positioned within the interior volume is also provided.

In a preferred form, an outwardly extending flange of either a pliant or a rigid material extends outwardly and terminates in a rim. The flange may be shaped to conform substantially to the breast or may be disc shaped as desired. The rim, the flange or both, can be provided with a pressure sensitive adhesive. The adhesive is preferably covered by a strip or sheet of release material prior to use. The pressure sensitive adhesive permits removable securement of the device to the breast while leaving a clinician with both hands free to operate the vacuum source or otherwise encourage a mammary fluid discharge, e.g., by manual massage of the breast.

The present device also includes an observation window. This window may be defined by the receptacle at a proximal end thereof. It is preferred that the window not magnify or otherwise distort the image of the nipple.

The illumination source preferably comprises a plurality of light emitting sources located about a proximal end of the hollow receptacle. These light emitting sources are preferably high-intensity lights, such as light emitting diodes (LED). The illumination enhances the practitioner's ability to identify a nipple orifice, and in particular, the nipple orifice from which a fluid sample is drawn.

The hollow receptacle and open aperture defined thereby are sized to accommodate the vast majority of nipple heights and circumferences. Preferably, the proximal end of the hollow receptacle is located approximately 1 inch (about 2.54 cm) away from the average nipple.

The particular vacuum port can be of any suitable configuration as is understood in the art for devices such as nipple aspirators and breast pumps. For example, the vacuum port can be attached to a three-way valve or an in-line one-way valve in a housing, such as a ball and spring, or a duckbill check valve. Similarly, the vacuum source can be any suitable source as is understood in the art for such nipple aspiration devices and breast pumps. For example, a tubing set and syringe may be coupled to the vacuum port to manually create a vacuum.

The device may also include one or more access ports if desired. The access port is located at the proximal end of the hollow receptacle. The access port is provided with a seal, such as a passive valve made from a rubber ring or gasket that is normally closed, i.e., when not accessed, and which closes automatically after access of the port by a medical instrument so as to maintain a substantially sealed environment. The access port can be used to provide access for a dilator, nipple orifice marker, catheter, biopsy brush, microendoscope, etc., while also maintaining a vacuum environment. As such, a particular nipple may be marked, probed or otherwise examined while illuminated and subject to a vacuum.

Another port can also be included to permit introduction of a warming liquid prior to activating the vacuum source. For example, warm water can be introduced into the device via the port and subsequently removed from the device via the vacuum port, a separate exhaust port or with a tool such as a pipette or syringe via an access port. A warming liquid serves to soften the nipple and increase blood flow and fluid mobility, thereby enhancing the aspiration of mammary duct fluid.

The device may also be configured without a vacuum port. With such a configuration, the device may be secured to a patient's breast and the breast manually manipulated to elicit a ductal discharge.

DESCRIPTION OF THE PREFERRED EMBODIMENT OF THE INVENTION

Figure 1:
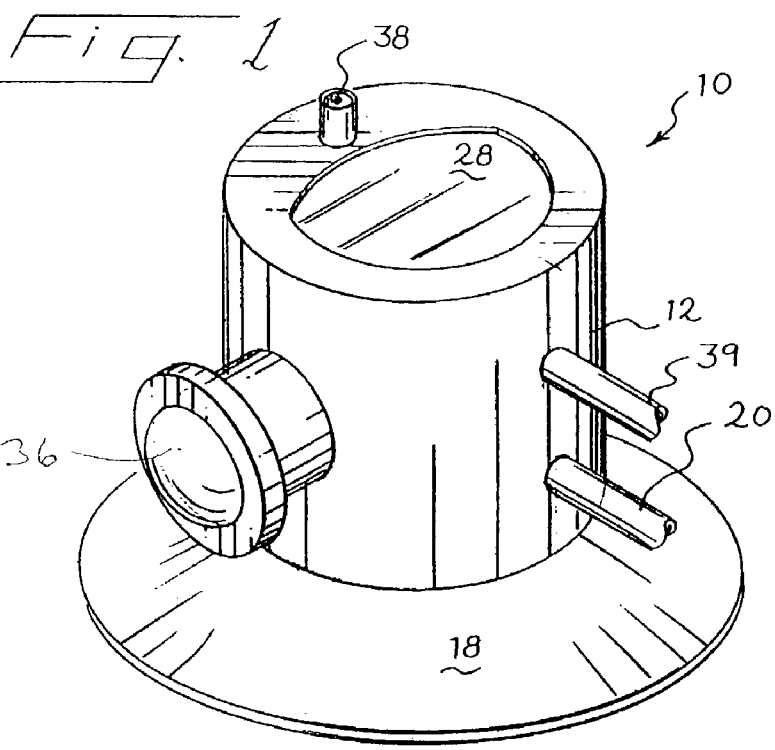
FIG. 1 is a perspective view of an embodiment of the present invention.

The invention disclosed herein is susceptible of embodiment in many different forms. Shown in the drawings and described hereinbelow in detail are preferred embodiments of the invention. It is to be understood, however, that the present disclosure is an exemplification of the principles of the invention and does not limit the invention to the illustrated embodiments.

Figure 2:
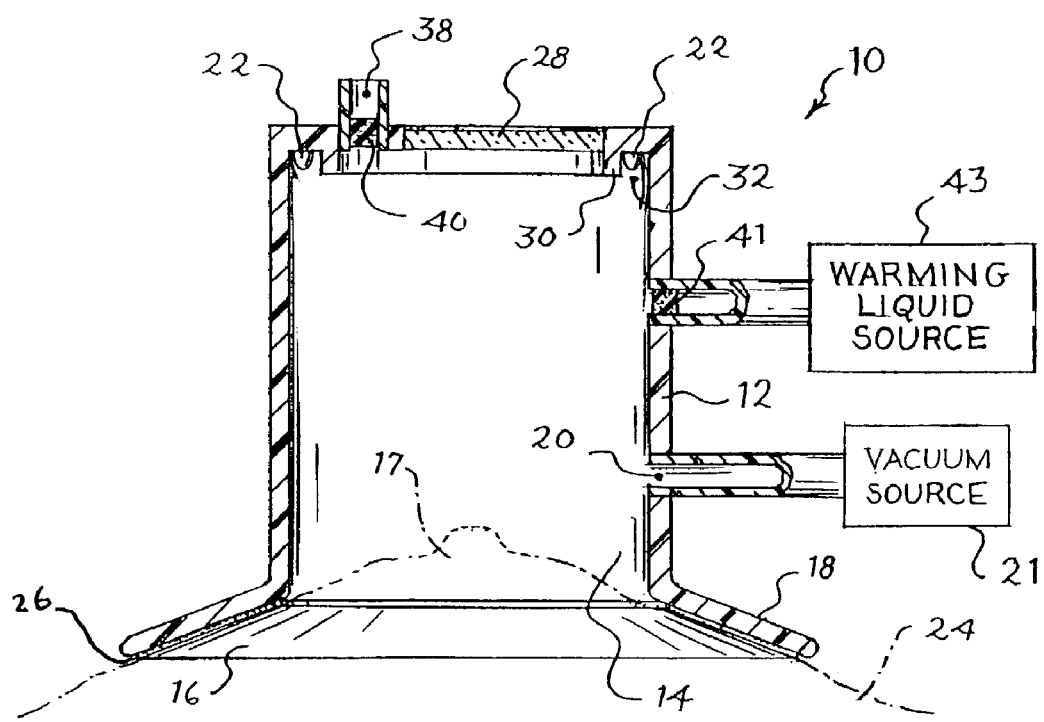
FIG. 2 is cross sectional side view of the device of FIG. 1.

Referring to FIGS. 1 and 2, device 10 comprises a hollow receptacle 12 defining an interior volume 14, and having an open aperture 16 sized to circumscribe the nipple 17. The open aperture 16 is defined by flange 18, which in turn terminates in rim 19. A vacuum port 20, which is suitable for connection to a vacuum source 21 to create a vacuum in the interior volume 14 is also formed with the hollow receptacle 12. An illumination source 22 to illuminate the nipple 17 within the interior volume 14 is also positioned within the hollow receptacle 12.

In a preferred form, the flange 18 of the device 10 made of either a pliant or rigid material. The flange 18 may be shaped to conform substantially to the breast 24, or may be disc shaped as desired. A pressure sensitive adhesive 26 is provided on the flange 18. Prior to use, the adhesive 26 is preferably covered by a strip or sheet of release material (not shown). The pressure sensitive adhesive 26 permits removable securement of the device 10 to the breast 24 while leaving the clinician with both hands free to operate the vacuum source 21.

An observation window 28 is situated at a proximal end of the hollow receptacle 12. The window 28 is preferably a non-distorting transparent rigid plastic material. The window 28 is also preferably circumscribed by rim 30, which defines inwardly extending flange or boss an open circular channel 32 having the illumination source 22 disposed therein.

Figure 3:
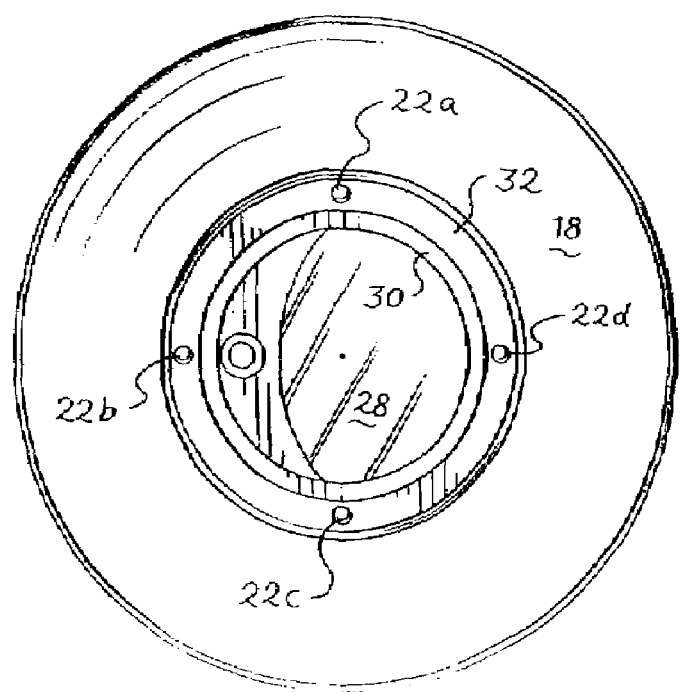
FIG. 3 bottom view of the device of FIG. 1.

The illumination source 22 preferably comprises a plurality of light emitting sources such as 22a, 22b, 22c, 22d as shown in FIG. 3. These light emitting sources are preferably high-intensity LED's. The LED's 22a, 22b, 22c, 22d are preferably battery powered such that no external power source is required. As shown in FIGS. 2 and 3, the LED's 22a, 22b, 22c, 22d are fully recessed within a channel 32, which is at least partially opaque to block light emitted in the direction of the window 28, which would undesirably cause a glare to the physician or other medical person. The LED's 22a, 22b, 22c, 22d are evenly spaced about the channel 32 so as to provide even illumination of the nipple and to minimize shadows on the nipple 17. The preferred number of individual light sources depends on the intensity of the particular sources used.

In use, device 10 is placed over a breast nipple, a vacuum source 21 is activated, and preferably causes at least one mammary duct to release fluid. While the fluid is being discharged, the illumination source 22 is activated. The activation of the illumination source 22 can occur in several ways. In one embodiment, a separate switch 36 can be operatively connected to the illumination source 22, and the physician or other medical person can turn on the illumination source 22. Alternatively, a switch may be operatively connected to the vacuum source or a valve, such that when the vacuum source is activated, the illumination source is likewise activated.

As discussed, it is preferred that the window 28 not visually distort the view of the nipple. For example, it is preferred that the window 28 not magnify the nipple area. Nipple heights can vary substantially from patient to patient. Similarly, the visual acuity of physicians is also highly variable. As such, the focal length of a generic magnifying lens may not be suitable for a particular patient or doctor. Indeed, in practice, it is preferred that the physician utilize a head mounted magnifying lens, if magnification is desired, which is fully adjustable to the particular patient and physician. Moreover, the same head mounted magnifying lens can be used in a variety of procedures or examinations.

The device may also include one or more access ports 38. In such a case, an access port 38 such as is preferably located at the proximal end of the hollow receptacle 12. The access port 38 is provided with a seal 40, such as a passive valve made from a rubber membrane that is closed when not accessed and which automatically closes when access of the port by a tool has been terminated. A catheter suitable to pick-up nipple aspirate for cytology evaluation would be a typical tool.

Another port 39 may also be provided, if desired, for introduction of a warming liquid such as water from a warming liquid source 43. The supplied liquid water is at a temperature above body temperature, usually at about 45° to about 55° centigrade, or higher. A seal 41 is also provided for port 39. A warming liquid can be introduced into the device via port 39 to soften the nipple and increase blood flow and mammary duct fluid mobility, thereby enhancing the subsequent aspiration of mammary duct fluid. The warming liquid can be vented and/or removed from the device via the vacuum port or an additional draining port can be provided for this purpose. For embodiments of this invention that include a warming liquid source, illumination source 22 is sealed to prevent exposure to the warming liquid. The warmed nipple can be dried prior to collection of a mammary fluid aspirate by circulating air utilizing the same ports.

During a medical procedure, the device 10 is placed over a nipple to be examined such that the open aperture 16 of hollow receptacle 10 circumscribes the patient's nipple 17. Prior to placing the device 10 on the patient, the adhesive 26 on rim 19 or flange 18 is exposed. As discussed, a warming liquid can be introduced. A syringe or other vacuum generating tool, shown schematically as vacuum source 21, is used to draw any warming liquid, as well as a portion of the air from the interior volume 14. The partial vacuum created through the removal of air can be about 250 mm Hg, or more, as desired. The present device is suitable to relatively higher vacuum levels pursuant to regulatory approval or when used under the guidance of qualified medical professional. As mammary fluid is drawn from one or more mammary ducts, inspection and identification of the corresponding nipple orifices may be more easily done under illumination provided by the illumination source 22.

Figure 4:
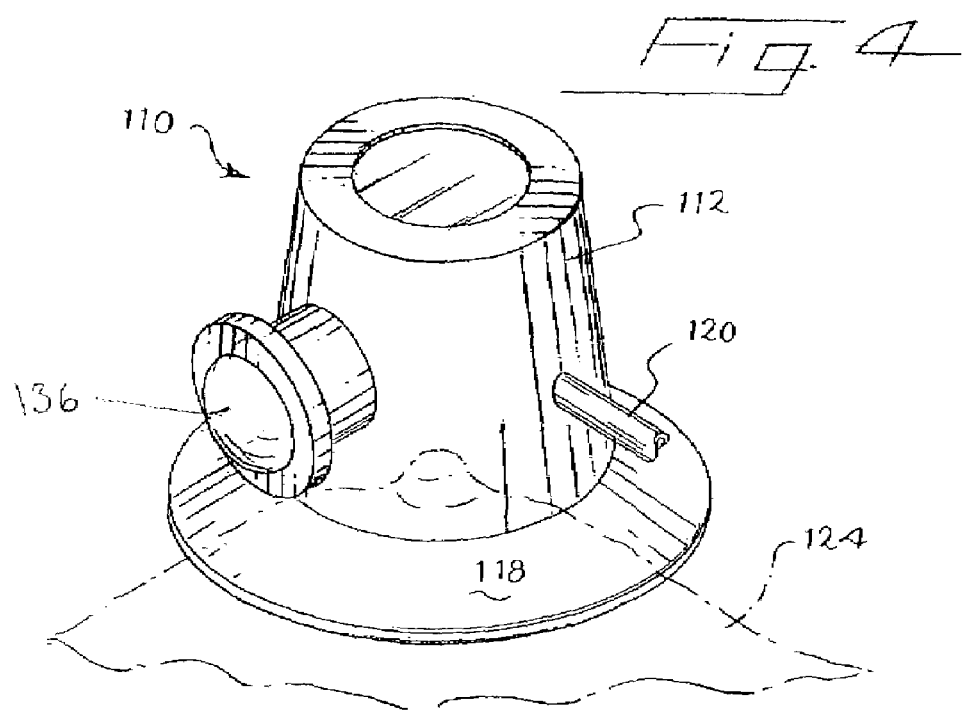
FIG. 4 a perspective view of an alternate embodiment of the present invention.
Figure 5:
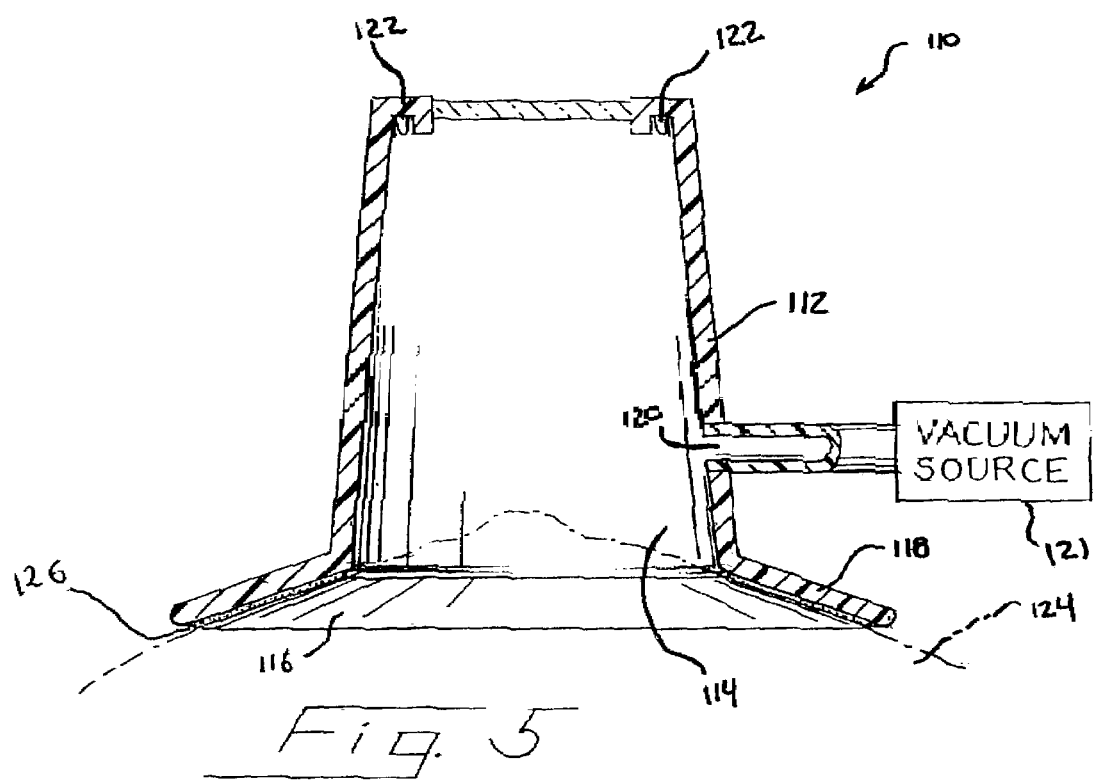
FIG. 5 is a cross sectional side view of the device of FIG. 4.

FIGS. 4 and 5 show an alternate embodiment of the present invention. Device 110 comprises a hollow receptacle 112, which defines an interior volume 114 and an open aperture 116 sized to circumscribe the nipple 117. The open aperture 116 is defined by a flange 118. A vacuum port 120, suitable for connection to a vacuum source 121, to create a vacuum in the interior volume 114 is also provided with the hollow receptacle 112. An illumination source 122 activated by switch 136 is also positioned within the hollow receptacle 112. Unlike the embodiment shown in FIGS. 1-3, in this particular embodiment the hollow receptacle 112 is configured in a frusto-conical shape such that the proximal end of hollow receptacle 112 is of a lesser diameter than the distal end. Such a configuration may be able to accommodate a greater variety of nipple areolas. Again, the flange 118 of the device 110 is of either a pliant or rigid material. The flange 118 may be shaped to conform substantially to the breast 124 or may be disc shaped as desired. The flange 118 is provided with a pressure sensitive adhesive 126. In this particular example, no access port or warming liquid port is shown. Such ports may be included, however, if desired.

The foregoing descriptions are to be taken as illustrative, but not limiting. Still other variants within the spirit and scope of the present invention will readily present themselves to those skilled in the art.

I claim:

1. A device suitable for viewing and illuminating a mammary duct orifice defined by a human breast nipple, the device comprising:
    a hollow receptacle defining an interior volume and having an open distal end sized to circumscribe the nipple;
    an observation window at a proximal end of the hollow receptacle;
    at least one access port;
    a warming port for introducing a warming agent into the interior volume;
    a vacuum port for connection to a vacuum source for creating a vacuum in the interior volume; and
    an illumination source mounted to the receptacle and to illuminate a nipple situated in the interior volume.

2. The device of claim 1, wherein the open distal end is surrounded by a flange.

3. The device of claim 2, wherein the flange is made of a rigid material.

4. The device of claim 2, wherein the flange is made of a pliant material.

5. The device of claim 2, wherein the flange includes a pressure sensitive adhesive disposed thereon for removable securement of the device to the human breast.

6. The device of claim 1, wherein the illumination source comprises a plurality of light emitting sources located within and about a proximal end of the hollow receptacle.

7. The device of claim 6, wherein the plurality of light emitting sources are located within a channel.

8. The device of claim 6, wherein the light emitting sources are light emitting diodes.

9. The device of claim 1, wherein the hollow receptacle is cylindrical.

10. The device of claim 1, wherein the hollow receptacle is frusto-conical.

11. The device of claim 1, wherein the at least one access port is located adjacent the observation window.

12. The device of claim 1, wherein the access port permits introduction of a tool.

13. The device of claim 1, further comprising a warming liquid source in operable association with the warming liquid port.

14. The device of claim 13 wherein the warming liquid source supplied liquid water at a temperature above body temperature.

15. The device of claim 1, further comprising a rim circumscribing the observation window.

16. A device suitable for viewing and illuminating a mammary duct orifice defined by a human breast nipple, the device comprising:
    a hollow receptacle defining an interior volume, and having an open aperture sized to circumscribe the nipple;
    an observation window at a proximal end of the hollow receptacle;
    an illumination source within the receptacle and positioned to illuminate the interior volume, the illumination source comprising a plurality of light emitting sources located about the observation window; and
    a warming liquid port.

17. The device of claim 16, further comprising a warming liquid source in operable association with the warming liquid port.

* * * * *